United States Patent
Raman et al.

(10) Patent No.: US 10,234,160 B2
(45) Date of Patent: Mar. 19, 2019

(54) SYSTEM AND METHOD FOR IDENTIFYING CO2 CONCENTRATION IN A BUILDING AREA

(71) Applicant: L&T TECHNOLOGY SERVICES LIMITED, Chennai (IN)

(72) Inventors: Krishnamoorthy Raman, Mysore (IN); Gineesh Sukumaran, Mysore (IN)

(73) Assignee: L&T TECHNOLOGY SERVICES LIMITED, Chennai (IN)

( * ) Notice: Subject to any disclaimer, the term of this patent is extended or adjusted under 35 U.S.C. 154(b) by 0 days.

(21) Appl. No.: 15/544,513

(22) PCT Filed: Aug. 13, 2015

(86) PCT No.: PCT/IB2015/056169
§ 371 (c)(1),
(2) Date: Jul. 18, 2017

(87) PCT Pub. No.: WO2016/116784
PCT Pub. Date: Jul. 28, 2016

(65) Prior Publication Data
US 2017/0370603 A1  Dec. 28, 2017

(30) Foreign Application Priority Data
Jan. 19, 2015 (IN) .............................. 276/CHE/2015

(51) Int. Cl.
*G06T 7/00* (2017.01)
*G01N 33/00* (2006.01)
(Continued)

(52) U.S. Cl.
CPC .......... *F24F 11/30* (2018.01); *F24F 11/0001* (2013.01); *F24F 11/62* (2018.01);
(Continued)

(58) Field of Classification Search
CPC ........ F24F 11/30; F24F 11/62; F24F 11/0001; F24F 2120/10; F24F 2110/70;
(Continued)

(56) References Cited

U.S. PATENT DOCUMENTS 7,369,955 B2   5/2008  Lee
8,715,202 B2 *  5/2014  Cardoso ............... G01N 33/497
                                                 250/339.13
(Continued)

OTHER PUBLICATIONS

Ogawa et al. "Monitoring Daily Activities and Behaviors at Home by Using Brief Sensors." Proceedings 1st Annual International IEEE-EMBS Special Topic Conference on Microtechnologies in Medicine and Biology, Oct. 12, 2000, pp. 611-614.*

*Primary Examiner* — Jon Chang
(74) *Attorney, Agent, or Firm* — Maschoff Brennan

(57) ABSTRACT

According to embodiments of the invention, a system 200 and method 100 for identifying $CO_2$ concentration in a building area using an imaging device 10 is disclosed. The disclosed method and system includes capturing the number of living beings present in a particular area of the building by the imaging device 10, identifying the active state of the living beings and categorizing the active state as per predefined criteria and identifying the $CO_2$ concentration based on the size of the building area, total number of living beings present in the building area and the active state of the living beings at a given point of time.

10 Claims, 2 Drawing Sheets

(51) Int. Cl.
*F24F 11/00* (2018.01)
*F24F 11/30* (2018.01)
*G06T 7/70* (2017.01)
*F24F 11/62* (2018.01)
*G05B 19/048* (2006.01)
*G05D 7/06* (2006.01)
*F24F 110/70* (2018.01)
*F24F 120/10* (2018.01)
*F24F 120/14* (2018.01)

(52) U.S. Cl.
CPC ......... *G01N 33/004* (2013.01); *G05B 19/048* (2013.01); *G05D 7/06* (2013.01); *G06T 7/70* (2017.01); *F24F 2011/0002* (2013.01); *F24F 2110/70* (2018.01); *F24F 2120/10* (2018.01); *F24F 2120/14* (2018.01); *G05B 2219/2614* (2013.01); *G06T 2207/30196* (2013.01); *G06T 2207/30242* (2013.01)

(58) Field of Classification Search
CPC . F24F 2120/14; F24F 2011/0002; G06T 7/70; G06T 2207/30196; G06T 2207/30242; G01N 33/004; G05B 19/048; G05B 2219/2614; G05D 7/06
See application file for complete search history.

(56) References Cited

U.S. PATENT DOCUMENTS

| | | | |
|---|---|---|---|
| 2003/0181158 A1* | 9/2003 | Schell | F24F 3/0442 454/229 |
| 2009/0143915 A1* | 6/2009 | Dougan | F24F 11/0001 700/276 |
| 2010/0040260 A1* | 2/2010 | Kelle | A01G 23/00 382/110 |
| 2012/0023976 A1* | 2/2012 | Kim | F24F 11/006 62/89 |
| 2013/0079658 A1 | 3/2013 | Cardoso et al. | |

* cited by examiner

SYSTEM AND METHOD FOR IDENTIFYING CO2 CONCENTRATION IN A BUILDING AREA

FIELD OF INVENTION

The invention generally relates to a system and method for identifying Carbon-dioxide ($CO_2$) level inside a building and particularly system and method for detecting Carbon-dioxide ($CO_2$) level inside a building through an imaging device.

BACKGROUND

Identification of Carbon dioxide ($CO_2$) level is critical and important function of a Heating/Ventilation/Air-conditioning (HVAC) duct system. Typically, for measuring carbon dioxide ($CO_2$) level, carbon dioxide ($CO_2$) detectors/sensors are employed in the building. Based on reading from the carbon dioxide ($CO_2$) detectors/sensors, the flow of fresh air can be increased or reduced into a particular part of the building.

Generally, $CO_2$ sensors for ventilation control are of two type i.e. photometric and photoacoustic. The photometric sensors have a sample compartment that contains a photo-detector, a light source and an optical filter. The light source emits light in the infrared range and the optical filter ensures that only wavelengths in the absorbing spectrum of $CO_2$ enter the compartment containing the air sample. The photodetector measures the light intensity at a wavelength that may be absorbed by $CO_2$. The higher the $CO_2$ concentration in the sample air, the lower the measured light intensity.

The photoacoustic sensors have a sample compartment that contains a microphone and a light source for emitting infrared energy. The $CO_2$ molecules in the compartment absorb the infrared energy, which in turn increases the molecular vibration and generates an acoustic field. The microphone picks up the acoustic field and converts it to an electronic signal identifying the $CO_2$ concentration.

However, known $CO_2$ detectors face one or more issues such as interference from other gases (e.g. water vapor), accuracy and drift that may affect the sensor performance. Moreover, $CO_2$ detectors are very costly, require periodic maintenance and are not very accurate. Therefore, there continues to be a need for maintenance free, cost effective and more accurate system and method for detecting $CO_2$ in a building.

The present invention is directed to overcoming one or more of the problems as set forth above.

SUMMARY OF THE INVENTION

According to embodiments of the invention, a system and method for identifying $CO_2$ concentration in a building area using an imaging device is disclosed. The disclosed method and system includes identifying the number of living beings present in a particular area of the building by processing images obtained from the imaging device; identifying the active state of the living beings and categorizing the active state as per predefined criteria; and identifying the $CO_2$ concentration based on the size of the building area, total number of living beings present in the building area and the active state of the living beings. The method may further include controlling the flow of fresh air by a HVAC system based on the $CO_2$ concentration.

The invention further discloses a system for identifying $CO_2$ concentration in a building area using an imaging device. The system may include a counting arrangement for counting number of living beings present in the building area by processing images obtained from an imaging device from the building area. The system may further include an activity analyses arrangement for identifying the active state of the living beings and categorizing the active state as per predefined criteria and a processor for calculating the $CO_2$ concentration in the building area based on the total number of living beings present in the building area and the active state of the living beings at a given point of time.

BRIEF DESCRIPTION OF DRAWINGS

Other objects, features, and advantages of the invention will be apparent from the following description when read with reference to the accompanying drawings. In the drawings, wherein like reference numerals denote corresponding parts throughout the several views.

DETAILED DESCRIPTION OF EXAMPLE EMBODIMENTS

Figure 1:
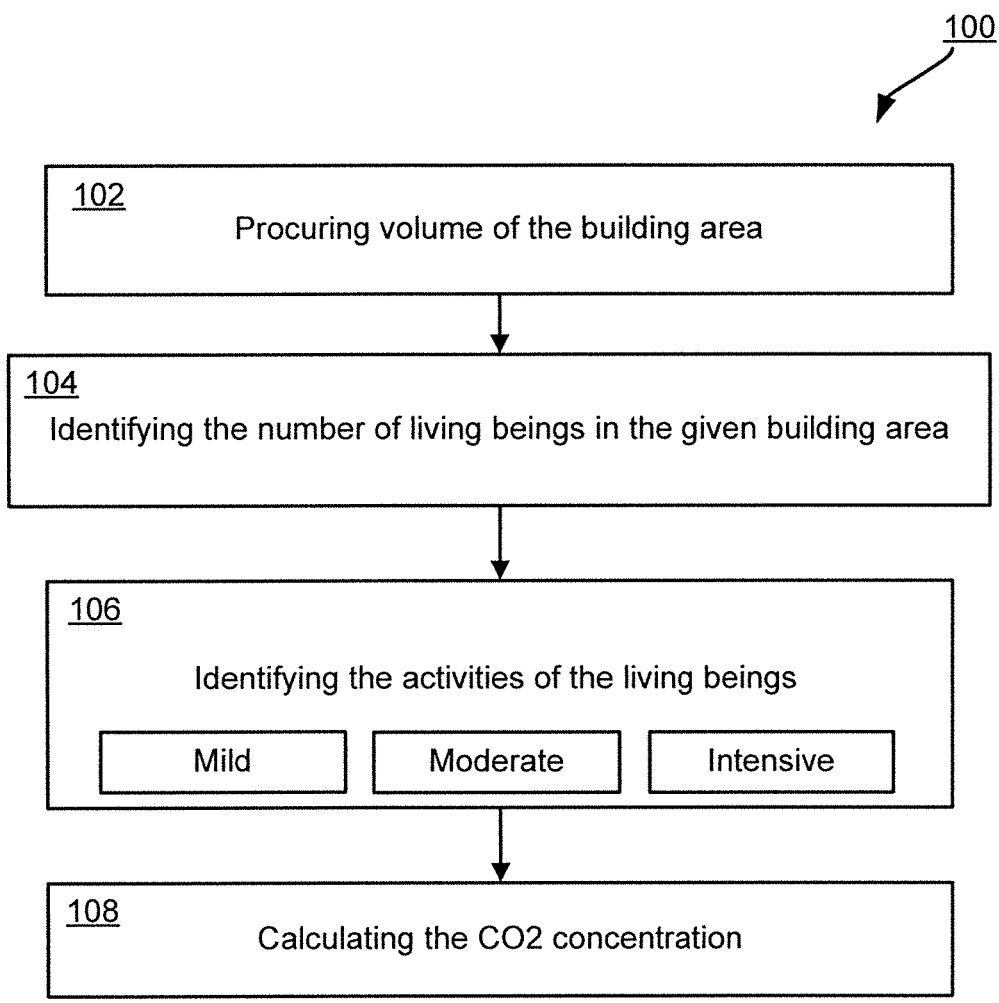
FIG. 1 illustrates an exemplary flow chart for a method for identifying $CO_2$ concentration in a building area according to an embodiment of the invention.

According to an embodiment of the invention, a method for detecting $CO_2$ in a building area using an imaging device is disclosed. The imaging device may be selected from a group comprising digital camera, web cam, overhead camera, security camera, spy camera etc. FIG. 1 illustrates an exemplary flow chart for a method 100 for identifying $CO_2$ concentration in a building area according to an embodiment of the invention. As illustrated at step 102 the method 100 includes procuring the volume of the building area where the concentration of $CO_2$ is required to be identified. According to an exemplary embodiment, the volume may be retrieved from a repository. According to yet another embodiment, the volume may be computed based dimensions of the building area.

At step 104, the method includes identifying number of living beings present in the given area. According to an embodiment, the number of living beings may be identified by keeping a count of incoming and outgoing living beings in the building area using live video feed from the imaging device. According to another embodiment, the number of living beings may be identified by analysing the images of the living beings in the area on real time basis.

According to yet another embodiment, the imaging device may perform a background modelling to eliminate noises due to illumination for effectively counting living beings in the building area. The background modelling involves detecting foreground objects and presenting the detected foreground objects to a binary classifier to distinguish the presence of living beings. According to an embodiment, the background modelling may be performed using any known methods for object detection such as but not limited to HAAR-Wavelet Transform, Gabor-Wavelet Transform, HAAR-Like Features, Histogram of Oriented Gradients etc.

According to an exemplary embodiment, to detect living being, either in static images or in videos, a frame may be identified. Once the frame is identified, the process of living being identification may be divided into two parts i.e. Feature Extraction and Classification. The feature extraction includes extracting unique feature from the captured image or video. According to an exemplary embodiment, any known technique for feature extraction such as, but not limited to, Haar-Wavelet Transform, Viola-Jones Haar-like Features, Histogram of oriented Gradients, Haar-Wavelet Transform may be used. The classification step may use classifiers. According to an embodiment of the invention, two types of classifiers may be used Neural Networks and/or Support Vector machine (SVM).

At step 106, the method includes identifying the active state of the living beings in the area. According to an embodiment, the active state of the living beings may be identified by processing the video images captured by the imaging device on real time basis. According another embodiment, the identified active state of the living beings may be categorized as mild such as, but not limited to, sitting, sleeping etc., moderate such as, but not limited to, walking, eating etc., intensive such as, but not limited to, playing, jumping, running etc. The invention is not restricted to disclosed three categories and the categories may vary and may be predefined a system administrator without going beyond the scope of invention.

According to an exemplary embodiment, the process of identifying the active state of the living beings includes, corner detection, optical flow and velocity thresholds. The corner detection includes identification of significant points in an image where gradient magnitude in both X & Y directions is significant or greater than a threshold. According yet another embodiment, any of the known corner detection algorithms may be used such as Harris Corner Detector, SIFT, SURF etc. The corners identified from the corner detection algorithms may include living beings, object of interest and static background scene. To distinguish or filter moving objects corners from static background corners an Optical Flow algorithm may be employed. The optical flow is the pattern of apparent motion of objects, surfaces, and edges in a visual scene caused by the relative motion between an observer (an eye or a camera) and the scene. Using the optical flow algorithm, the direction and speed of moving objects from one image to another image may be measured in terms of velocity vectors. A predefined velocity threshold may be employed to separate moving objects corners from rest of the corners (corners of slow moving background objects like tree branches, Static Object corners and false velocity measures caused by illumination effects) in the consecutive frames.

To classify actions as mild, moderate or intensive the velocity of each corner in an image or frame may be identified. The velocity of the corners may be compared with the predefined velocity threshold. Based on the comparison, the motion of the objects may be categorised as still, mild, moderate or intensive. According to an embodiment, the amount of $CO_2$ generation by the living beings may vary based on the activity classification. According to another embodiment, the activity classification may be predefined in the system or may be procured on a real time basis through a network such as internet, intranet etc.

Table 1 below illustrate exemplary relation between carbon dioxide emission from persons and their activity:

TABLE 1

| Activity | Respiration per Person ($m^3$/h) | Carbon Dioxide Emission per Person ($m^3$/h) |
|---|---|---|
| Sleep | 0.3 | 0.013 |
| Resting or low activity work | 0.5 | 0.02 |

TABLE 1-continued

| Activity | Respiration per Person ($m^3$/h) | Carbon Dioxide Emission per Person ($m^3$/h) |
|---|---|---|
| Normal work | 2-3 | 0.08-0.13 |
| Hard work | 7-8 | 0.33-0.38 |

At step 108, the method calculates $CO_2$ concentration as a function of volume of the area, number of living beings present in the area and activities of the living beings present in the area as illustrated below:

$$\kappa_{CO_2} = f(N_p, A_p, V_r)$$

Where $N_p$ is the number of living beings present in the area, $A_p$ is the active state of the living beings present in the area and $V_r$ is the volume of the area.

Exemplary considering, imaging device identify N number of living being in a building area having volume V. On processing images from the imaging device, it is identified that out of N number of living being N1 living beings are engaged in mild activity, N2 living beings are engaged in moderate activities and N3 living beings are engaged in intensive activities.

$$Np = N1 + N2 + N3$$

The total activity factor for the total number of people in the room $An_p$ may be calculated as:

$$An_p = N1*x + N2*y + N3*z$$

Where x, y and z are predefined constant for mild, moderate or intensive activities respectively. According yet another embodiment, the number of predefined activity constant is equal to the number of predefined active states. According yet another embodiment, the total activity factor $An_p$ indicates the total $CO_2$ generated by the living beings present in the building area per hour. The amount of $CO_2$ generated in ppm per minute may be calculated using following equation:

$$\kappa_{CO_2} = \frac{An_p * 60 * 10^3}{V_r}$$

According to another embodiment, for calculating the total concentration of $CO_2$ in the building area, apart from $CO_2$ generated, ventilation rate and $CO_2$ concentration outside building area may also be considered.

According to yet another embodiment based on $CO_2$ concentration the air circulation system of a HVAC system may be controlled.

According to an embodiment, the method steps may be performed in any sequence without going beyond the essence of the invention. According to another embodiment, the method may process all the functions simultaneously.

Figure 2:
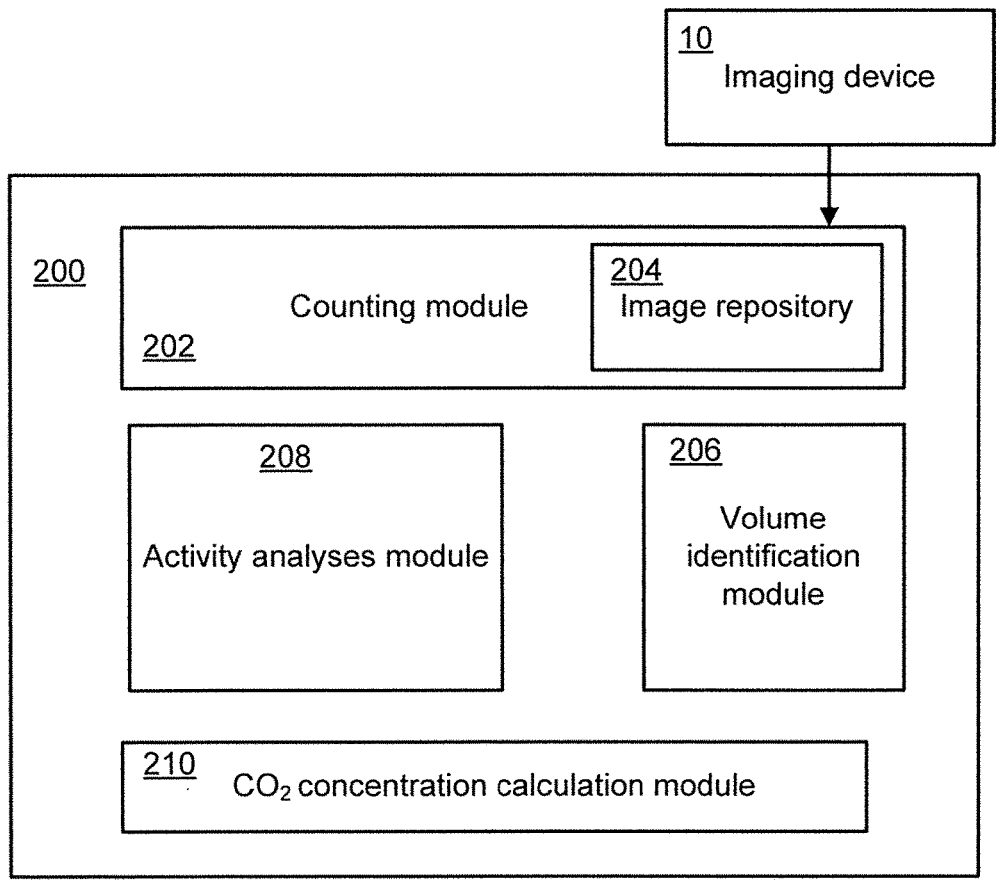
FIG. 2 illustrates an exemplary system for identifying $CO_2$ concentration in a building area according to another embodiment of the invention.

FIG. 2 illustrates an exemplary block diagram of the system 200 for identifying $CO_2$ concentration in a building area according to an embodiment of the invention. The system 200 may be configured to receive images from an imaging device 10. The imaging device 10 may be any apparatus for capturing images such as but not limited to a digital video camera, web cam, overhead camera, spy cam etc. The system 200 may include a counting module 202 for counting number of living beings present in the building area. According to an embodiment, the counting module 202 may identify the number of living beings by processing images obtained from the imaging device. According to another embodiment, the images received from the imaging device 10 may be stored in an image repository 204 for further processing. The images may include still images and/or video images.

According to an embodiment, the counting module 202 may identify the number of living beings by processing the images to count the number of incoming and outgoing living beings from the building area. According to yet another embodiment, the counting module 202 may identify the number of living beings by analysing the images of the living beings in the area on real time basis.

The system 200 may have a volume identification module 206 for procuring the volume of the building where the concentration of $CO_2$ is required to be detected. According to an embodiment, the volume may be retrieved from a repository. According to yet another embodiment, the volume may be computed based on dimensions of the area procured from the images.

The system 200 may further include an activity analyses module 208 for identifying the active state of the living beings present in the building area. The activity analyses module 208 may further categorize the active state of the living beings as per predefined criteria. According to an embodiment, the activity analyses module 208 may identify the active state of the living beings by processing the images captured by the imaging device 10 on real time basis. According to another embodiment, the identified active state of the living beings may be categorized as mild, moderate or intensive by the activity analyses module 208. According to yet another embodiment, the invention is not restricted to disclosed three categories and it may vary without going beyond the scope of invention.

The system 200 may further have a module 210 for identifying the $CO_2$ concentration in the building area. The module 210 may identify $CO_2$ concentration as a function of volume of the area $V_r$, number of living beings present in the area $N_p$ and the activities of the living beings present in the area.

According to an embodiment, the system 200 may have an inbuilt imaging device 10. According to another embodiment, the counting module 202, the volume identification module 206, the activity analyses module 208 and the $CO_2$ concentration calculation module 210 may reside in different processors. According to yet another embodiment, the counting module 202, the volume identification module 206, the activity analyses module 208 and the $CO_2$ concentration calculation module 210 may reside in a single processor.

In the foregoing detailed description of embodiments of the invention, various features are grouped together in a single embodiment for the purpose of streamlining the disclosure. This method of disclosure is not to be interpreted as reflecting an intention that the claimed embodiments of the invention require more features than are expressly recited in each claim. Rather, as the following claims reflect, inventive subject matter lies in less than all features of a single disclosed embodiment. Thus, the following claims are hereby incorporated into the detailed description of embodiments of the invention, with each claim standing on its own as a separate embodiment.

It is understood that the above description is intended to be illustrative, and not restrictive. It is intended to cover all alternatives, modifications and equivalents as may be included within the spirit and scope of the invention as defined in the appended claims. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein," respectively.

We claim:

1. A method for identifying $CO_2$ concentration in a building area using an imaging device, the method comprising:
   obtaining the number of living beings present in a particular area of the building by processing images obtained from the imaging device;
   identifying the active state of the living beings from the images and categorizing the active state as per predefined criteria; and
   computing the $CO_2$ concentration based on the total number of living beings, the active state of the living beings and the size of the building area.

2. The method as claimed in claim 1, wherein the predefined criteria for categorizing the active state of the living beings comprises categories of active state as mild, moderate or intensive.

3. The method as claimed in claim 1, wherein the number of living beings is identified by an algorithm selected from HAAR-Wavelet Transform, Gabor-Wavelet Transform, HAAR-Like Features or Histogram of Oriented Gradients.

4. The-method as claimed in claim 1, further comprising controlling the flow of fresh air by an HVAC system based on the $CO_2$ concentration.

5. A system for identifying $CO_2$ concentration in a building area using an imaging device, the system comprising:
   a counting module for counting the number of people from the images obtained by the imaging device,
   an activity analyses module for identifying the active state of the living beings by processing images obtained by the imaging device and categorizing the active state as per predefined criteria; and
   a $CO_2$ concentration calculation module for calculating the $CO_2$ concentration based on information obtained from the counting module, the activity analyses module and a volume identification module.

6. The system as claimed in claim 5, wherein the predefined criteria for categorizing the active state of the living beings comprises categories of active state as mild, moderate or intensive.

7. The system as claimed in claim 5, further comprising controlling the flow of fresh air by an HVAC system based on the $CO_2$ concentration.

8. The system as claimed in claim 5, further comprising an imaging device.

9. The system as claimed in claim 5, wherein the volume identification module identifies the volume of the building where the concentration of $CO_2$ is required to be detected based on dimensions of the area procured from the images.

10. An imaging device comprising:
    a counting module for counting the number of people from the images obtained by the imaging device,
    an activity analyses module for identifying the active slate of the living beings by processing images obtained by the imaging device and categorizing the active state as per predefined criteria; and
    a $CO_2$ concentration calculation module for calculating the $CO_2$ concentration based on information obtained from the counting module, the activity analyses module and a volume identification module.

\* \* \* \* \*